United States Patent [19]

Worley et al.

[11] Patent Number: 5,057,612

[45] Date of Patent: Oct. 15, 1991

[54] N,N'-DIHALOIMIDAZOLIDIN-4-ONES

[75] Inventors: Shelby D. Worley; Techen Tsao, both of Auburn; Delbert E. Williams, Waverly, all of Ala.

[73] Assignee: Auburn Research Foundation, Auburn, Ala.

[21] Appl. No.: 467,929

[22] Filed: Jan. 22, 1990

[51] Int. Cl.$^5$ .......................................... C07C 233/20
[52] U.S. Cl. .................................................. 548/301
[58] Field of Search ........................................ 548/301

[56] References Cited

PUBLICATIONS

Tsao, T. C. et al., Novel N–halamine Disinfectant Cmpds, Biotechnology Progress, vol. 7(1), pp. 60–66, 1991.

Primary Examiner—Mary C. Lee
Assistant Examiner—Peter Davis
Attorney, Agent, or Firm—Thad G. Long

[57] ABSTRACT

Substituted N-halo derivatives of imidazolidin-4-ones having substituents at the 2 and 5 positions of the imidazolidin-4-one ring are described. More particularly, there are described N-chloro, N-bromo, N,N'-dichloro, N,N'-dibromo, and N,N'-bromochloro derivatives of imidazolidin-4-ones having substituents selected from hydrogen, alkyl, alkoxy, hydroxy, phenyl, substituted phenyl, or spiro-substitution at the 2 and 5 positions on the ring. These N-halo compounds are stable, noncorrosive biocides which are resistant to direct sunlight, and are useful as disinfectants, sanitizers, and algae inhibitors.

31 Claims, No Drawings

N,N'-DIHALOIMIDAZOLIDIN-4-ONES

INTRODUCTION

The present invention addresses the problem of disinfection of water which might be used in potable water supplies, swimming pools, hot tubs, industrial water systems, cooling towers, waste water treatment plants, toilet bowls, air conditioning systems, spacecraft, military field units, and in other sanitizing applications, as well as of organic fluids such as oils, and of hard surfaces in hospitals, food processing plants, and other facilities where microbiological contamination is a problem.

Current disinfectants which are in use for the above-mentioned purposes all have serious limitations. The most widely used commercial disinfectants are sources of "free halogen"—chlorine, bromine, or iodine—such as calcium or sodium hypochlorite or chlorine gas. Although free halogen is known to be an effective disinfectant, it does have numerous deleterious properties. It is corrosive to many materials, and for this reason it cannot be used for long-term applications such as sanitization of cooling water in closed-cycle circulatory systems such as large air conditioning units, thus prohibiting its use as an effective biocide for *Legionella pneumophila*, the cause of Legionaires disease. It causes the rapid deterioration of the filters in the reverse osmosis water treatment units employed by the military in field water sanitization. Furthermore, free halogen is very reactive with organic contaminants in water leading to the production of toxic trihalomethanes such as chloroform which have been linked to cancer in laboratory animals. Chlorine or bromine in swimming pools can cause considerable irritation to the skin or eyes of people susceptible to its deleterious effects. Free halogen is quite unstable in water, particularly in water exposed to sunlight such as in swimming pools, necessitating the addition of substantial quantities of stabilizers such as cyanuric acid which may be deleterious themselves in high concentration.

On the other hand, much more stable sources of "combined halogen" such as the oxazolidinones (Kaminski et al., U.S. Pat. Nos. 4,000,293 and 3,931,213; S.D. Worley et al., U.S. Pat. No. 4,659,484) and N,N'-dihalo-2-imidazolidinones (S.D. Worley, U.S. Pat. Nos. 4,681,948 and 4,767,542), which do not suffer the limitations mentioned above, release little, or no, free halogen and generally require long contact times to kill microorganisms in water.

There is a great need for a general-purpose, broad-spectrum disinfectant which is stable over extended time periods, which does not react appreciably with materials causing corrosion or the production of toxic trihalomethanes, and which is biocidal in reasonable contact times. In other words, a halogen source is needed which possesses the desirable attributes of both free halogen and combined halogen in sanitization applications. In a broad aspect of the present invention, the N,N'-dihaloimidazolidin-4-ones fulfill this purpose. They are stable crystalline solids which impart minimal color, odor, or taste to water at biocidal concentrations (1 to 10 milligrams per liter total halogen) and are intermediate in disinfection time and persistence between free halogen and the combined halamines mentioned above. They are also much easier to synthesize than the previous oxazolidinone or imidazolidinone series, utilizing completely different synthetic methods, which should render them commercially feasible.

DETAILED DESCRIPTION OF THE INVENTION

The novel N,N'-dihaloimidazolidin-4-ones and N-haloimidazolidin-4-ones described herein are heterocyclic organic compounds that may be represented by the graphic formula illustrated below:

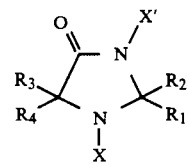

wherein X and X' are each halogen, selected from the group consisting of chlorine, bromine, and mixtures thereof, or either X or X' may be hydrogen, while the other is halogen selected from the group chlorine and bromine; and wherein $R_1$, $R_2$, $R_3$, and $R_4$ are each selected from the group consisting of hydrogen, $C_1$-$C_4$ alkyl, $C_1$-$C_4$ alkoxy, hydroxy, phenyl, and substituted phenyl, or $R_1$, $R_2$ and/or $R_3$, $R_4$ may represent spiro-substitution selected from the group consisting of pentamethylene and tetramethylene, and mixtures thereof; provided, however, that not more than three of the substituents $R_1$-$R_4$ are methyl when X is chlorine and X' is hydrogen.

The alkyl substituents attached to the ring of the imidazolidin-4-one compounds or to the phenyl substituent or to oxygen as alkoxy groups may contain from 1 to 4 carbon atoms; namely, methyl, ethyl, propyl, isopropyl, and the butyls, eg., n-butyl, isobutyl, secondary butyl, and tertiary butyl. Spiro-substitution at the $R_1$, $R_2$ substituted ring carbon or at the $R_3$, $R_4$ carbon or at both of these substituted ring carbons will consist of the pentamethylene or tetramethylene moieties.

Examples of the aforedescribed compounds include but are not limited to: 1,3-dichloro-2,2,5,5-tetramethylimidazolidin-4-one; 1-bromo-3-chloro-2,2,5,5-tetramethylimidazolidin-4-one; 1,3-dibromo-2,2,5,5-tetramethylimidazolidin-4-one; 1,3-dichloro-2,5-bis(pentamethylene)imidazolidin-4-one; 1,3-dichloro-2-pentamethylene-5,5-dimethylimidazolidin-4-one; 1,3-dichloro-2,2-dimethyl-5-pentamethyleneimidazolidin-4-one; 1,3-dichloro-2,2,5-trimethyl-5-ethylimidazolidin-4-one; and 1,3-dichloro-2-hydroxy-2,5,5-trimethylimidazolidin-4-one.

By substitution of other named substituents for $R_1$-$R_4$, e.g. ethyl, propyl, butyl, methoxy, ethoxy, propoxy, hydroxy, para-methylphenyl, etc., for one or more of the derivatives above named, other correspondingly named N,N'-dichloro-, dibromo-, or bromo-chloro- imidazolidin-4-one derivatives may be named.

N,N'-dihaloimidazolidin-4-one derivatives of the present invention may be prepared by reacting the corresponding unhalogenated imidazolidin-4-one or imidazolidine-4-thione with a source of chlorine, bromine, or, in the case of the 1-bromo-3-chloro derivatives, first a source of bromine and then a source of chlorine or in the case of the 1-chloro-3-bromo derivatives, first a source of chlorine and then a source of bromine. While chlorine gas or liquid bromine may be utilized, other milder halogenating agents such as N-chlorosuccinimide, N-bromosuccinimide, sodium dichloroisocyanurate, trichloroisocyanuric acid, calcium hypochlorite, sodium hypochlorite, tertiary butyl hypochlorite, N-chloroacetamide, N-chloramines, N-bromamines, etc., may also be employed. Halogenation of the unhalogenated imidazolidin-4-ones or imidazolidine-4-thiones may be accomplished in aqueous media or in mixtures of water with common inert organic solvents such as methylene chloride, chloroform, and carbon tetrachloride, at room temperatures. Inert organic solvents may be used alone with the N,N'-dihaloimidazolidin-4-one compounds.

Unhalogenated imidazolidine-4-thiones can be prepared by reacting 2 moles disubstituted ketone, e.g. acetone, with 1 mole sodium cyanide, 1.3 moles ammonium sulfide, and 1 mole ammonium chloride to form, e.g. 2,2,5,5-tetramethylimidazolidine-4-thione in a manner similar to that described by J. D. Christian in the article, "4-Imidazolidinethiones", *J. Org. Chem.*, 22, 396 (1957). Unhalogenated imidazolidin-4-ones, e.g. 2,2,5,5-tetramethylimidazolidin-4-one, can be prepared by oxidation of the corresponding unhalogenated imidazolidine-4-thione with hydrogen peroxide under alkaline conditions as described by P. G. Ferrini and A. Marxer in the article "Chemotherapeutic Studies in the Heterocyclic Series. XLI. Unexpected Reaction by Treatment of 2,2,5,5-Tetramethylimidazolidine-4-thione with Nitric Acid", *Helv. Chem. Acta*, 46, 1207 (1963). It is contemplated that other imidazolidine-4-thione or imidazolidin-4-one derivatives can be synthesized from the corresponding dialkyl ketone, and subsequent oxidation for the latter, or by other organic synthetic routes known to those skilled in the art. For example, it is contemplated that 1,3-dichloro-2,5-bis(pentamethylene)imidazolidin-4-one may be prepared by reacting 2 moles of cyclohexanone with 1 mole sodium cyanide, 1.3 moles ammonium sulfide, and 1 mole ammonium chloride, followed by chlorination or by oxidation with hydrogen peroxide in basic solution and then chlorination.

Halogenated derivatives of substituted imidazolidin-4-one may be employed as disinfectants against undesirable microorganisms in aqueous as well as other solution media by treating the media with a biocidally effective amount of the imidazolidin-4-one compound. The imidazolidin-4-one compounds useful for disinfection applications contemplated herein may be represented by the graphic formula:

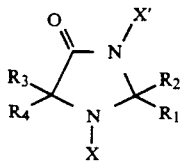

II wherein X and X' are each halogen selected from the group consisting of chlorine and bromine, or either X or X' may be hydrogen, while the other is halogen selected from the group chlorine and bromine, and wherein $R_1$, $R_2$, $R_3$, and $R_4$ are each selected from the group consisting of hydrogen, $C_1$-$C_4$ alkyl, $C_1$-$C_4$ alkoxy, hydroxy, phenyl, and substituted phenyl, or $R_1$, $R_2$ and/or $R_3$, $R_4$ may represent spiro-substitution selected from the group consisting of pentamethylene and tetramethylene, and mixtures thereof; provided, however, that not more than one of the substituents $R_1$-$R_4$ is hydrogen. The compound 1-chloro-2,2,5,5-tetramethylimidazolidin-4-one is not novel, having been prepared by T. Toda, E. Nori, H. Horiuchi, and K. Murayama and used as a source of amino radicals in an electron spin resonance experiment, but not as a disinfectant, as described in the article "Studies on Stable Free Radicals. X. Photolysis of Hindered N-Chloramines", *Bull. Chem. Soc. Japan*, 45, 1802 (1972).

The halogenated imidazolidin-4-one derivatives described herein for use as disinfectants may be used in combination with other sources of active disinfecting halogen, e.g., chlorine or bromine. Examples of other sources of disinfecting halogen include, but are not limited to, chlorine gas, bromine liquid, sodium hypochlorite, calcium hypochlorite, tertiary butyl hypochlorite, N-chlorosuccinimide, N-bromosuccinimide, N,N'-dihalodimethylhydantoins, trichloroisocyanuric acid, sodium or potassium salts of N-halohydantoins or N,N'-dihalocyanurates, N-halo-2-oxazolidinones, N-haloglycolurils, and N,N'-dihalo-2-imidazolidinones. Such additional sources of active halogen may be used prior to, subsequent to, or simultaneously with the use of the aforesaid imidazolidin-4-one derivatives.

In a further embodiment of the present invention, it is contemplated that the aqueous or other solution media may be disinfected by introducing into the media (a) a nonhalogenated or monohalogenated imidazolidin-4-one corresponding to the compounds of graphic formula II, ie. compounds represented by graphic formula III:

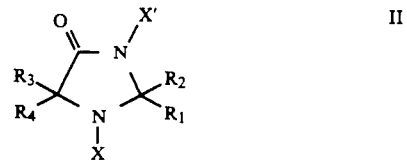

II wherein X and X' are selected from the group hydrogen, chlorine, and bromine; provided that at least one must be hydrogen; and wherein $R_1$, $R_2$, $R_3$, and $R_4$ are each selected from the group consisting of hydrogen, $C_1$-$C_4$ alkyl, $C_1$-$C_4$ alkoxy, hydroxy, phenyl, and substituted phenyl, or $R_1$,$R_2$ and/or $R_3$,$R_4$ may represent spiro-substitution selected from the group consisting of pentamethylene and tetramethylene, and mixtures thereof; provided, however, that not more than one of the substituents $R_1$-$R_4$ is hydrogen, and (b) at least a stoichiometric amount of a source of halogen selected from the group consisting of chlorine and bromine, whereby to form in situ a biocidal amount of the corresponding N,N'-dlhaloimidazolidin-4-one or 1-haloimidazolidin-4-one or 3-haloimidazolidin-4-one derivative. Sources of chlorine and bromine that may be employed include, but are not limited to, chlorine gas, bromine liquid, sodium hypochlorite, calcium hypochlorite, tertiary butyl hypochlorite, and N-halogenated compounds which release their halogen in aqueous or other solution media and which are less stable under the disinfection conditions than the N,N'-dihaloimidazolidin-4-one formed in situ, e.g., N,N'-dihalohydantoins and trichloroisocyanuric acid.

Generally, enough N,N'-dihaloimidazolidin-4-one or N-haloimidazolidin-4-one (preformed or formed in situ) of graphic formula II or III is used to provide about 0.3 to 10 milligrams of potential positive halogen, e.g., chlorine, per liter of solution to provide a biocidal effect in the solution. The amount of potential positive halogen, e.g., chlorine, furnished by the halogenated imidazolidin-4-one derivative corresponds to the theoretical amount of halogen that is available from the derivative used, or between 1 and 60 mg per liter of solution of halogenated imidazolidin-4-one is generally used to provide a biocidal amount.

All microorganisms in aqueous or other solutions or on hard surfaces susceptible to disinfection by free halogen, e.g., free chlorine, will also be susceptible to disinfection by the halogenated imidazolidin-4-one derivatives, such as bacteria, protozoa, fungi, viruses, and algae. Of the more prominent microorganisms susceptible to disinfection by the halogenated imidazolidin-4-one derivatives, there may be mentioned bacteria such as *Staphylococcus aureus, Pseudomonas aeruginosa, Shigella boydii, Salmonella enteritidis,* and *Legionella pneumophila;* protozoa such as *Giardia lamblia;* fungi such as *Candida albicans;* viruses such as herpesvirus and rotavirus; and algae such as *Anabaena cylindrica, Oscillatoria lutea,* and *Chlorella pyrenoidosa.* The amount of halogenated imidazolidin-4-one derivative required to inactivate a bacterium in its environment may be described as a bactericidal amount. Similarly, when the organism is a protozoa, virus, or fungus, the amount of halogenated imidazolidin-4-one derivative required is termed a protozoacidal, virucidal, or fungicidal amount. In the case of algae, the amount of halogenated imidazolidin-4-one derivative may be expressed as an algaestatic amount rather than as an algacidal amount, for the halogenated imidazolidin-4-one derivatives are effective at preventing the growth of algae in aqueous solution.

The halogenated imidazolidin-4-one derivatives described herein may be employed in a variety of bleaching, disinfecting, sanitizing, and other biocidal applications. It is contemplated that they will be of particular importance in controlling microbiological contamination of swimming pools and hot tubs. The long-term stability of the compounds will allow them to disinfect over extended time periods without frequent replenishment. The unhalogenated or monohalogenated imidazolidin-4-one derivatives will be of use as "stabilizers" for free halogen in that mixtures of free halogen and the derivatives will exist in the form of the halogenated derivatives in situ. Thus a mixture of unhalogenated imidazolidin-4-one derivative with free halogen will prevent the growth of algae in a swimming pool for extended time periods with occassional addition of free halogen to the pool. The halogenated imidazolidin-4-one derivatives are much more stable in the presence of direct sunlight than are known sources of free halogen such as the N-halo-hydantoins and N-halo-isocyanurates, and can thus be considered as sources of "stabilized" halogen. The halogenated imidazolidin-4-one derivatives will prevent the growth of undesirable organisms such as *Legionella pneumophila*, algae, and sources of biofouling in closed-cycle cooling water systems. The exceptional stability of the compounds at elevated temperatures, e.g., 37° C., will render them useful for disinfection of hot tubs and food products. The mild, noncorrosive natures of the compounds will make them useful as sanitizers for hard surfaces, e.g., in hospitals and for toilet bowls. They should find widespread use as disinfectants in the food processing industry and for sterile detergents for dishwashing in restaurants.

The halogenated and unhalogenated imidazolidin-4-one derivatives described herein may be used in diverse liquid and solid formulations such as powders, granular materials, solutions, concentrates, emulsions, slurries, and in the presence of diluents, entenders, fillers, conditioners, aqueous solvent, organic solvents, and the like. Of particular use may be their employment in formulations involving wetting, emulsifying, or dispersing agents such as sulfonates, alkanols, alcohols, or other similar surface active materials. The compounds are also compatible with buffering agents and other sources of halogen.

The present invention is more particularly described in the following examples which are intended as illustrative only since numerous modifications and variations therein will be apparent to those skilled in the art.

EXAMPLE 1

Preparation of 2,2,5,5-tetramethylimidazolidine-4-thione

In a 1 liter flask a solution of 14.7 grams (0.3 mole) sodium cyanide, 16.1 grams (0.3 mole) ammonium chloride, and 111.4 grams of 23.8% aqueous ammonium sulfide (0.39 mole) in 80 milliliters of water was prepared. 34.8 Grams (0.6 mole) of acetone was added slowly over a 20–30 minute period with stirring. The contents of the reaction flask were then stirred for 6 hours at a temperature of 55°–70° C. produced by means of a heated water bath. The flask containing the reaction products was then cooled in an ice bath causing the precipitation of the 2,2,5,5-tetramethylimidazolidine-4-thione. The solid product was recovered by suction filtration, and further product was recovered upon suction filtration after concentration of the aqueous solution by evacuation. The solid was purified by recrystallization from a mixture of 20 parts water to 1 part acetone. The total product yield was 46.0 grams or 97% of that theoretically expected. The product was found to have a melting point range of 153°–154° C.

EXAMPLE 2

Preparation of 2,2,5,5-tetramethylimidazolidin-4-one 15.8 Grams (0.1 mole) of the thione product from example 1 was added to 125 milliliters of 2 Normal sodium hydroxide solution in a 500 milliliter flask. Then 57 milliliters of 30% hydrogen peroxide was added over a 30–40 minute period at 5°–10° C. while stirring with the flask in an ice bath. The reaction mixture was then allowed to stand at ambient temperature for 2 hours. The solution was evaporated to dryness, and the solid 2,2,5,5-tetramethylimidazolidin-4-one product was recrystallized from isopropyl alcohol. The total product yield was 14.2 grams or 90% of that theoretically expected. The product was found to have a melting point range of 169°–170° C.

EXAMPLE 3

Preparation of 1,3-Dichloro-2,2,5,5-tetramethylimidazolidin-4-one

This product was prepared by two methods: (a) chlorination of the thione prepared as in example 1 with chlorine serving as oxidant and halogenating agent and (b) chlorination of the ketone prepared as in example 2.

In method (a) 47.4 grams (0.3 mole) of 2,2,5,5-tetramethylimidazolidine-4-thione was dissolved in 1.2 liters of 3 Normal sodium hydroxide solution (3.6 moles) in a 2 liter flask. The flask and its contents were cooled to 5° C. using an ice bath, and chlorine gas was bubbled into the mixture while stirring until the pH of the solution reached 7.0. The temperature of the mixture was not allowed to rise above 10° C. during this process. The N,N'-dichloroimidazolidin-4-one product precipitated as a white solid. Following addition of 800 milliliters of water to the flask, the solid product was recovered by suction filtration. The product was then purified by dissolving it in hexane, allowing the impurities and remaining water to settle, and recovery by evaporation of the volatile hexane layer which was separated from the impurity/water layer. The product yield was 53.9 grams or 85% of that theoretically expected. Elemental analysis of the product (1,3-dichloro-2,2,5,5-tetramethylimidazolidin-4-one) gave the following results: (calculated/found) % carbon 39.82/39.86, % hydrogen 5.73/5.50, % nitrogen 13.27/13.24, and % chlorine 33.59/32.88. The product was found to have a solubility in water ranging from 0.138 grams in 100 milliliters of water at 3° C. to 0.224 grams in 100 milliliters of water at 37° C. The product had a melting point range of 69°-71° C. Analysis of the product by proton NMR and infrared spectroscopy yielded the following results: $^1$H NMR (CCl$_4$) $\delta = 1.36$ (S,6H), $\delta = 1.50$ (S,6H); IR (KBr) 1720, 2950 cm$^{-1}$.

In method (b) 5.1 grams (0.036 mole) of 2,2,5,5-tetramethylimidazolidin-4-one was dissolved in 88 milliliters of 1 Normal sodium hydroxide (0.088 mole) in a 250 milliliter flask. The flask and its contents were placed into an ice bath, and chlorine gas was bubbled into the mixture while stirring and maintaining the temperature below 10° C. until a pH of 7.0 was reached. The N,N'-dichloroimidazolidin-4-one product precipitated as a white solid. The product was recovered by suction filtration and was purified by recrystallization from hexane. It possessed the same properties as those determined for the product obtained in method (a). The yield was 6.9 grams or 91% of that theoretically expected.

EXAMPLE 4

Preparation of
1,3-Dibromo-2,2,5,5-tetramethylimidazolidin-4-one 5.1 Grams (0.036 mole) of 2,2,5,5-tetramethylimidazolidin-4-one prepared as in example 2 was dissolved in 88 milliliters of 1 Normal sodium hydroxide solution (0.088 mole) in a 250 milliliter flask. While maintaining this mixture at 10° C. or below using an ice bath and stirring, 12.8 grams (0.08 mole) of liquid bromine was added dropwise. The product, 1,3-dibromo-2,2,5,5-tetramethylimidazolidin-4-one precipitated from the mixture as a pale yellow solid. The product was recovered by suction filtration and purified by recrystallization from hexane. The product yield was 9.2 grams or 85% of that theoretically expected. Elemental analysis of the product (1,3-dibromo-2,2,5,5-tetramethylimidazolidin-4-one) gave the following results: (calculated/found) % carbon 28.00/27.80, % hydrogen 4.00/4.07, % nitrogen 9.33/9.39, and % bromine 53.33/52.09. The product was found to have a solubility in water ranging from 0.072 grams in 100 milliliters of water at 3° C. to 0.120 grams in 100 milliliters of water at 37° C. The product had a melting point range of 109°-111° C. Analysis of the product by proton NMR and infrared spectroscopy yielded the following results: $^1$H NMR (CCl$_4$) $\delta = 1.35$ (S,6H), $\delta = 1.51$ (S,6H); IR (KBr) 1725,2965 cm$^{-1}$.

EXAMPLE 5

Preparation of
1-Bromo-3-chloro-2,2,5,5-tetramethylimidazolidin-4-one 6.4 Grams (0.045 mole) of 2,2,5,5-tetramethylimidazolidin-4-one prepared as in example 2 was dissolved in 55 milliliters of 1 Normal sodium hydroxide solution (0.055 mole) in a 250 milliliter flask. While maintaining the reaction mixture at a temperature of 5°-10° C. by use of an ice bath and stirring, 4.0 grams (0.025 mole) of liquid bromine was added dropwise. The reaction mixture was stirred at ice bath temperature for an additional 1 hour and then for 1-2 hours at cold water bath conditions (10°-20° C.). Following cooling the mixture below 10° C. again, 50 milliliters of 1 Normal sodium hydroxide solution (0.05 mole) was added, and chlorine gas was bubbled in while stirring at 5°-10° C. until the pH reached 6-7. The 1-bromo-3-chloro-2,2,5,5-tetramethylimidazolidin-4-one product precipitated as a white solid. The product was recovered by suction filtration and purified by recrystallization from hexane. The product yield was 11.2 grams or 97% of that theoretically expected. Elemental analysis of the product gave the following results: (calculated/found) % carbon 32.88/32.68, % hydrogen 4.70/4.74, % nitrogen 10.96/10.83, % bromine 31.31/33.37, % chlorine 13.89/12.67. The rather high and low found values as compared to the theoretical values for bromine and chlorine, respectively, indicate that the product was contaminated with a small amount of 1,3-dibromo-2,2,5,5-tetramethylimidazolidin-4-one. The product was found to have a solubility in water ranging from 0.102 grams in 100 milliliters of water at 3° C. to 0.193 grams in 100 milliliters of water at 37° C. The product had a melting point of 88° C.±2° C. Analysis of the product by proton NMR and infrared spectroscopy yielded the following results: $^1$H NMR (CCl$_4$) $\delta = 1.34$ (S,6H), $\delta = 1.50$ (S,6H); IR (KBr) 1700, 2950 cm$^{-1}$.

EXAMPLE 6

Preparation of
1-chloro-2,2,5,5-tetramethylimidazolidin-4-one 14.2 Grams (0.1 mole) of 2,2,5,5-tetramethylimidazolidin-4-one prepared as in example 2 was dissolved in 100 milliliters of 1 Normal sodium hydroxide solution (0.1 mole) in a 250 milliliter flask. The flask containing the mixture was placed in an ice bath and maintained at or below 10° C. with stirring while chlorine gas was bubbled in until the pH reached 7.0. The product 1-chloro-2,2,5,5-tetramethylimidazolidin-4-one which precipitated as a white solid was recovered by suction filtration and was purified by recrystallization from an ether/hexane mixture. The product yield was 17.7 grams or 95% of that theoretically expected. The product had a melting point range of 157.0°-157.5° C. Analysis of the product by proton NMR and IR spectroscopy yielded the following results: $^1$H NMR (CDCl$_3$) $\delta = 1.32$ (S,6H), $\delta = 1.46$ (S,6H), $\delta = 7.57$ (Broad,1H); IR (KBr) 1670, 1720, 3160 cm$^{-1}$.

EXAMPLE 7

Formation of N-Halogenated Imidazolidin-4-ones In Situ

An aqueous solution containing 50.0 milligrams (3.52×10$^{-4}$ moles) of 2,2,5,5-tetramethylimidazolidin- 4-one synthesized as in example 2 in 50.0 milliliters of 0.05 molar sodium phosphate buffer (pH 7.0) was prepared. The buffer solution had been made halogen demand-free by chlorination with 3 milligrams per liter total chlorine from sodium hypochlorite followed by exposure to direct sunlight for two days until no titratable chlorine remained. A halogen demand-free solution of free chlorine buffered to pH 7.0 was prepared by bubbling chlorine gas into a flask containing the demand-free buffered water. Then 19 milliliters of the solution containing 1.31 grams per liter of free chlorine ($7.02 \times 10^{-4}$ moles of positive halogen) was added to the solution containing the 2,2,5,5-tetramethylimidazolidin-4-one at ambient temperature ($24°\pm1°$ C.) while stirring.

The reaction rate for formation of 1,3-dichloro-2,2,5,5-tetramethylimidazolidin-4-one and/or 1-chloro-2,2,5,5-tetramethylimidazolidin-4-one in situ was then followed kinetically by observing the loss of free chlorine concentration from the reaction mixture as a function of time. The concentration of free chlorine was monitored by withdrawing aliquots from the mixture periodically and titrating them by the DPD/FAS (N,N-diethyl-p-phenylenediamine/ferrous ammonium sulfate) method as described in "Standard Methods for the Examination of Water and Wastewater, 16th edition, American Public Health Association, Washington, D.C., 1985, pp. 306-309. The moles of free chlorine present in the reaction mixture declined from $7.02 \times 10^{-4}$ at the time of mixing to $4.45 \times 10^{-5}$ after only 48 seconds representing 94% reaction. Then further declination of free chlorine occurred to $3.63 \times 10^{-5}$ moles after 2.87 minutes, $3.48 \times 10^{-5}$ moles after 6.07 minutes, and $3.32 \times 10^{-5}$ moles after 114.6 minutes. Thus after 114.6 minutes 95% of the reaction had occurred. At this time $1.76 \times 10^{-5}$ additional moles of 2,2,5,5-tetramethylimidazolidin-4-one was added, and the concentration of free chlorine declined to zero by 140 minutes total elapsed time.

The data indicate that the 2,2,5,5-tetramethylimidazolidin-4-one contained a small amount of inert impurities (less than or equal 5%), and although the proportion of dichloro and monochloro imidazolidin-4-one was not determined, that the halogenated imidazolidin-4-ones form efficiently and rapidly (less than 1 minute) in situ when free chlorine is added to pH 7.0 demand-free water containing the unhalogenated 2,2,5,5-tetramethylimidazolidin-4-one.

EXAMPLE 8

Hydrolysis Equilibrium Constant for 1,3-Dichloro-2,2,5,5-tetramethylimidazolidin-4-one The equilibrium constant for the hydrolysis reaction of 1,3-dichloro-2,2,5,5-tetramethylimidazolidin-4-one to form 1-chloro-2,2,5,5-tetramethylimidazolidin-4-one and free chlorine ($Cl^+$) was determined at pH 7.0 and $24°\pm1°$ C. This was accomplished by preparing a solution of the 1,3-dichloro-2,2,5,5-tetramethylimidazolidin-4-one in demand-free 0.05 molar sodium phosphate buffer (pH 7.0) and allowing the solution to equilibrate while stirring for 1 hour. Then the DPD/FAS technique (as in example 7) was used to determine the free and total chlorine concentrations in the equilibrated solution. The concentration of combined 1,3-dichloro-2,2,5,5-tetramethylimidazolidin-4-one was calculated from the difference between the measured total and free chlorine concentrations. The hydrolysis equilibrium constant was then calculated as the square of the molar free chlorine concentration divided by the molar combined chlorine concentration. For a starting molar total chlorine concentration of $4.441 \times 10^{-3}$ moles per liter, at equilibrium the combined chlorine concentration was $4.428 \times 10^{-3}$ moles per liter, and the free chlorine concentration was $1.269 \times 10^{-5}$ moles per liter. These data give a hydrolysis equilibrium constant for the dichloroimidazolidin-4-one of $3.64 \times 10^{-8}$. For a starting molar total chlorine concentration of $1.764 \times 10^{-3}$ moles per liter, at equilibrium the combined chlorine concentration was $1.759 \times 10^{-3}$ moles per liter, and the free chlorine concentration was $5.360 \times 10^{-6}$ moles per liter. These data give a hydrolysis equilibrium constant of $1.63 \times 10^{-8}$. The average equilibrium constant for the two separate determinations was thus $2.6 \pm 1.0 \times 10^{-8}$.

This value for the hydrolysis equilibrium constant for 1,3-dichloro-2,2,5,5-tetramethylimidazolidin-4-one is much lower than those reported for the commercial N-halamines dichlorodimethylhydantoin ($2.54 \times 10^{-4}$) and trichloroisocyanuric acid ($1.6 \times 10^{-4}$) (G. D. Nelson, "Chloramines and Bromamines", Kirk-Othmer Encyclopedia of Chemical Technology, 3rd ed., vol. 5, Wiley Interscience, New York, 1979, p. 565).

On the other hand, the value is a bit higher than that reported for the commercial N-halamine 3-chloro-4,4-dimethyl-2-oxazolidinone ($2.3 \times 10^{-9}$) by D. E. Williams, E. D. Elder, and S. D. Worley in an article entitled "Is Free Halogen Necessary for Disinfection?", *Appl. Environ. Microbiol.*, 54, 2583 (1988).

From these results it is expected that 1,3-dichloro-2,2,5,5-tetramethylimidazolidinone should be considerably more stable in water at pH 7.0 than dichlorodimethylhydantoin and trichloroisocyanuric acid, but somewhat less stable than 3-chloro-4,4-dimethyl-2-oxazolidinone. This should be beneficial in its use because dichlorodimethylhydantoin and trichloroisocyanuric acid have limited stability in aqueous solution, needing to be replenished frequently, while 3-chloro-4,4-dimethyl-2-oxazolidinone is so stable that it liberates almost no free chlorine, rendering it a very slow-acting biocide. The new dihalogenated imidazolidin-4-one should breach the gap between these two extremes.

EXAMPLE 9

Laboratory Stability of 1,3-Dichloro-2,2,5,5-tetramethylimidazolidin-4-one

The stability of 1,3-dichloro-2,2,5,5-tetramethylimidazolidin-4-one(Compound 1) in halogen demand-free water determined at 22° C. and pH values of 4.5, 7.0, and 9.5, and the results were compared to those for free chlorine as supplied by calcium hypochlorite. The demand-free water (DFW) was prepared by chlorination of distilled, deionized water buffered to the appropriate pH followed by dechlorination (of the excess free chlorine) by exposure to direct sunlight until no free chlorine remained. This treatment insured that all halogen demand in the water was neutralized. Then Compound 1 and calcium hypochlorite were separately dissolved in identical DFW (buffered to an appropriate pH) solutions to the same final total chlorine concentrations (10 milligrams per liter potential positive chlorine). The solutions in separate flasks, which were stoppered with porous, sterile cotton plugs to allow free exchange with laboratory air, were then held at a constant temperature of 22° C. by means of a controlled water bath for a period of several weeks. Aliquots were withdrawn periodically (at least weekly), and the total positive chlorine remaining was determined in triplicate by standard iodometric titration. Results are tabulated in Table I.

TABLE I

| | Percent Chlorine Remaining Temp. = 22° C. | | | | | |
|---|---|---|---|---|---|---|
| | pH | | | | | |
| | 4.5[a] | | 7.0[b] | | 9.5[c] | |
| Time, Wks. | Compound | | | | | |
| | 1 | 2 | 1 | 2 | 1 | 2 |
| 0.14 | 100.0 | ND | ND | ND | 96.5 | ND |
| 0.57 | 88.9 | ND | ND | ND | 98.9 | ND |
| 1 | 77.6 | 91.8 | 97.1 | 91.8 | 95.1 | 88.9 |
| 2 | 55.5 | 86.2 | 95.0 | 85.0 | 89.4 | 79.0 |
| 3 | 40.4 | 80.8 | 93.5 | 79.6 | 82.6 | 71.2 |
| 4 | 30.7 | 76.4 | 90.6 | 70.6 | 72.3 | 60.3 |
| 5 | 26.0 | 71.5 | 86.0 | 63.4 | 63.7 | 50.1 |
| 6 | 23.5 | 65.0[d] | 83.4 | 54.7[d] | 55.1 | 385[d] |

[a]0.05 Molar Acetate Buffer
[b]0.05 Molar Phosphate Buffer
[c]0.01 Molar Borate/NaOH Buffer
[d]6.14 weeks
1 = 1,3-dichloro-2,2,5,5-tetramethylimidazolidin-4-one
2 = Free Chlorine from Calcium Hypochlorite
ND = No Determination The data of Table I demonstrate that Compound 1 is considerably more stable in DFW at pH 7.0 at 22° C. than is free chlorine. Compound 1 is also more stable than free chlorine in alkaline DFW (pH 9.5). However, Compound 1 is rather unstable in acidic DFW (pH 4.5), which indicates that the imidazolidin-4-one ring most likely undergoes decomposition at low pH. For most disinfection applications the pH is held at 7.0 or higher under which conditions Compound 1 is more stable than free chlorine in DFW.

EXAMPLE 10

Laboratory Stability of 1-Chloro-2,2,5,5-tetramethylimidazolidin-4-one

The hydrolysis product of 1,3-dichloro-2,2,5,5-tetramethylimidazolidin-4-one is 1-chloro-2,2,5,5-tetramethylimidazolidin-4-one (see example 8). The stability of the monochloroimidazolidin-4-one in demand-free water (DFW) at pH 7.0 and 22° C. was determined in a manner analogous to the procedure described in example 9. Thus 1-chloro-2,2,5,5-tetramethylimidazolidin-4-one (Compound 3) prepared as in example 6 was dissolved in DFW buffered at pH 7.0 so as to obtain a starting total potential positive chlorine concentration of 10 milligrams per liter. The solution was analyzed weekly as described in example 9. The results showed that the total potential positive chlorine content declined very slowly over a 7 week period with 89.0% remaining after the 7 week period. This performance demonstrates that Compound 3 is more stable than Compound 1 and considerably more stable than free chlorine (Compound 2) in DFW at pH 7.0 and 22° C. (see also data in example 9).

EXAMPLE 11

Laboratory Stabilities of 1,3-dioromo-2,2,5,5-tetramethylimidazolidin-4-one and 1-bromo-3-chloro-2,2,5,5-tetramethylimidazolidin-4-one The stabilities of 1,3-dibromo-2,2,5,5-tetramethylimidazolidin-4-one (Compound 4) and 1-bromo-3-chloro-2,2,5,5-tetramethylimidazolidin-4-one (Compound 5) in halogen demand-free water (DFW) were determined at 22° C. and pH values of 7.0 and 9.5 using the same procedures as discussed under example 9. Given the instability of Compound 1 at pH 4.5 (example 9), it was deemed unnecessary to test compounds 4 and 5 at that pH. The two compounds were dissolved in DFW buffered to the appropriate pH in separate flasks and held at a temperature of 22° C. by means of a constant temperature bath. The starting concentrations of total potential positive halogen in the two solutions were 22.6 milligrams per liter for Compound 4 and 16.25 milligrams per liter for Compound 5; these concentrations represent the molar equivalents in total potential positive halogen to that used for Compound 1 in example 9. The solutions were analyzed in the manner described in example 9. Results are tabulated along with those for Compound 1 for comparison in Table II.

TABLE II

| | Percent Chlorine Remaining | | | | | |
|---|---|---|---|---|---|---|
| | pH | | | | | |
| | 7.0[a] | | | 9.5[b] | | |
| Time, Wks. | Compound | | | | | |
| | 1 | 4 | 5 | 1 | 4 | 5 |
| 0.14 | ND | ND | 97.3 | 96.5 | 91.4 | 96.3 |
| 0.71 | ND | ND | 95.4 | ND | 71.0[c] | 89.5 |
| 1 | 97.1 | ND | 91.7 | 95.1 | 36.0 | 88.3 |
| 2 | 95.0 | ND | 88.2 | 89.4 | 4.8 | 86.3 |
| 3 | 93.5 | ND | 75.0 | 82.6 | ND | 70.8 |
| 4 | 90.6 | ND | 45.9 | 72.3 | ND | 60.8 |
| 5 | 86.0 | ND | 17.5 | 63.7 | ND | 46.8 |
| 6 | 83.4 | ND | 7.6 | 55.1 | ND | 38.4 |

[a]0.05 Molar Phosphate Buffer
[b]0.01 Molar Borate/NaOH Buffer
[c]0.43 Weeks
1 = 1,3-dichloro-2,2,5,5-tetramethylimidazolidin-4-one
4 = 1,3-dibromo-2,2,5,5-tetramethylimidazolidin-4-one
5 = 1-bromo-3-chloro-2,2,5,5-tetramethylimidazolidin-4-one
ND = No Determination The data of Table II demonstrate that Compound 1 is considerably more stable in DFW at pH values of 7.0 and 9.5 and 22° C. than are Compounds 4 and 5. Compound 5 is comparable in stability to free chlorine (see data in example 9) at pH 9.5 only.

EXAMPLE 12

Stabilities of Haloimidazolidin-4-one Derivatives in Water Containing Heavy Halogen Demand A synthetic halogen demand water (SDW) was prepared by mixing the following substances with demand-free water (DFW): 375 milligrams per liter of each of the inorganic salts sodium chloride, potassium chloride, calcium chloride, and magnesium chloride; 50 milligrams per liter of Bentonite clay; 30 milligrams per liter of humic acid; 0.01 percent final concentration of heat-treated horse serum; and 5×10[5] cells per milliliter of heat-killed *Saccharomyces cerevisiae* yeast cells. The SDW solution was buffered with 0.01 Molar borate/sodium hydroxide to a pH of 9.5 and held at 4° C. during the experiments. The conditions of high ionic strength, turbidity, and organic material, and alkaline pH at low temperature, are viewed as a worst-case scenario for disinfection applications and thus should provide the optimum test of stability for the new compounds.

In separate flasks were dissolved compounds 1, 2, 3, and 5 to a starting concentration of 10 milligrams per liter total potential positive chlorine or its molar equivalent (16.25 milligrams per liter) in total potential positive halogen for Compound 5. Aliquots were withdrawn frequently over a period of more than 90 hours, and the percent positive halogen remaining was determined by standard iodometric titration. Results are tabulated in Table III.

TABLE III

Percent Halogen Remaining in Synthetic Demand Water
Temp. = 4° C.; pH = 9.5

| Time, Hrs. | Compound | | | |
|---|---|---|---|---|
| | 1 | 2 | 3 | 5 |
| 0.008 | ND | ND | ND | 64.0 |
| 0.083 | 98.8 | ND | 99.2 | ND |
| 0.167 | ND | ND | ND | 49.9 |
| 0.25 | 98.8 | ND | ND | ND |
| 0.5 | 93.1 | 51.5 | 96.6 | 47.1 |
| 1.0 | 92.4 | 46.4 | ND | 47.4 |
| 2.0 | 92.4 | ND | 95.4 | ND |
| 2.5 | ND | 39.6 | ND | ND |
| 4.0 | 88.8 | ND | ND | 41.9 |
| 4.2 | ND | 39.6 | ND | ND |
| 7.5 | ND | 36.2 | ND | ND |
| 8.0 | ND | ND | 94.1 | ND |
| 24.0 | ND | 31.3 | 94.9 | 38.2 |
| 25.0 | 71.4 | ND | ND | ND |
| 48.0 | ND | ND | 94.5 | ND |
| 72.0 | ND | ND | 94.1 | ND |
| 76.5 | ND | 21.5 | ND | ND |
| 93.0 | 60.2 | ND | ND | ND |
| 94.0 | ND | ND | ND | 31.8 |
| 122.0 | ND | ND | 94.1 | ND |

1 = 1,3-dichloro-2,2,5,5-tetramethylimidazolidin-4-one
2 = Free Chlorine from Calcium Hypochlorite
3 = 1-chloro-2,2,5,5-tetramethylimidazolidin-4-one
5 = 1-bromo-3-chloro-2,2,5,5-tetramethylimidazolidin-4-one The data of Table III demonstrate that Compound 3 is extremely stable in the presence of heavy demand while Compound 1 is also much more stable under these conditions than is free chlorine. Compound 5 is comparable in stability to free chlorine under these conditions.

EXAMPLE 13

Stability of N,N'-dihaloimidazolidin-4-ones in Water Exposed to Direct Sunlight

The stabilities of compounds 1,5, and free chlorine from calcium hypochlorite (Compound 2) in water exposed to direct sunlight were determined. Each compound at the 10 milligrams per liter total chlorine concentration level (or at the molar equivalent for total halogen for Compound 5) was dissolved in 85 milliliters of demand-free water buffered at pH 7.0 in separate 100 milliliter beakers which were placed in a temperature-controlled water bath (22°-24° C.), and the bath containing the solutions was placed on the roof of the chemistry building at Auburn University exposed to direct sunlight during August 1988. Total potential positive halogen assays were made periodically on aliquots withdrawn over a 10 hour period using the standard iodometric titration technique. The results are tabulated in Table IV.

TABLE IV

Percent Halogen Remaining in Demand Free Water Exposed to Direct Sunlight
Temp. = 22-24° C.; pH = 7.0

| Time, Hrs. | Compound | | |
|---|---|---|---|
| | 1 | 2 | 5 |
| 3.0 | 84.9 | 26.0 | 60.5 |
| 5.0 | 74.8 | 6.9 | 45.7 |
| 10.0 | 51.2 | 0.0 | 14.9 |

1 = 1,3-dichloro-2,2,5,5-tetramethylimidazolidin-4-one
2 = Free Chlorine from Calcium Hypochlorite
5 = 1-bromo-3-chloro-2,2,5,5-tetramethylimidazolidin-4-one The data of Table IV demonstrate that Compound 1 is much more stable than free chlorine at pH 7.0 and 22°-24° C. in the presence of direct sunlight. Compound 5 is less stable than Compound 1, but significantly more stable than free chlorine, under these conditions.

EXAMPLE 14

The Stability of 2,2,5,5-tetramethylimidazolidin-4-one in Water Exposed to Direct Sunlight A solution containing 142 milligrams ($1.00 \times 10^{-3}$ moles) of 2,2,5,5-tetramethylimidazolidin-4-one (Compound 6) in 1.0 liter of demand-free water buffered to pH 7.0 was prepared. 100 milliliter samples ($1.00 \times 10^{-4}$ moles of Compound 6) of this solution were placed in each of five 100 milliliter volumetric flasks. The flasks were sealed with ground glass stoppers and placed in direct sunlight on the roof of the chemistry building at Auburn University during the period July 6, 1989 to Aug. 2, 1989. No effort was made to control the temperature in this experiment; it was typically 33° C. during this period. At time zero and at subsequent 7 day intervals flasks were removed from the direct sunlight, and the solutions were reacted with a slight excess of free chlorine ($2.2 \times 10^{-4}$ moles which was prepared by bubbling chlorine gas into buffered demand-free water as described in example 7.

After allowing the reaction of Compound 6 with free chlorine to form a mixture of 1,3-dichloro-2,2,5,5-tetramethylimidazolidin-4-one (Compound 1) and 1-chloro-2,2,5,5-tetramethylimidazolidin-4-one (Compound 3) to proceed with stirring over a period of 1 hour, aliquots were analyzed for total and free chlorine using the DPD-FAS procedure mentioned in example 8. The combined chlorine concentration was assumed to be the difference between the determined total and free chlorine concentrations, and to represent the amounts of compounds 1 and 3 forming during the reaction.

It was found that the combined chlorine concentration varied by less than or equal 6 percent during the course of the 4 week experiment. In fact it was actually determined to be higher after 4 weeks of exposure to direct sunlight than at time zero, indicating that variations were due entirely to experimental error in the analytical procedure, and not to decomposition of Compound 6 caused by direct sunlight. These data demonstrate that the compound 2,2,5,5-tetramethylimidazolidin-4-one, which is the precursor to the chlorinated imidazolidin-4-ones, is stable in demand-free water solution at pH 7.0 exposed to direct sunlight for at least 4 weeks. Thus this compound should be useful for long-term, in situ, outdoor halogenation applications.

EXAMPLE 15

Bactericidal Efficacies of the Halogenated Imidazolidin-4-ones

The halogenated imidazolidin-4-one derivatives prepared as in examples 3, 5, and 6 (Compounds 1, 5, and 3, respectively) were tested as bactericides against the microorganisms Staphylococcus aureus (ATCC 25923) and Pseudomonas aeruginosa (ATCC 27853) in demand-free water (DFW) as a function of pH and temperature and in a synthetic-demand water (SDW) at pH 9.5 and 4° C. The demand-free and synthetic-demand waters were prepared as described in examples 7 and 12, respectively.

For the bactericidal efficacy tests 50 milliliters of buffered DFW or SDW were placed in a 125 milliliter flask which was then inoculated with the organism to be tested such that the final density of the organism was about $1 \times 10^6$ cfu/ml (colony forming units per milliliter). The inoculated solution was allowed to equilibrate at the test temperature by immersion in a thermostated water bath for 15 minutes with constant stirring. Then an appropriate amount of an aqueous solution containing the test halogenated imidazolidin-4-one compound maintained at the same test temperature was added to the inoculated solution to bring the total concentration of potential positive halogen (Cl+ or Cl+/Br+) in the mixture to a predetermined level (10 parts per million and 5 parts per million Cl+ from compounds 1 and 3; the molar equivalent in Cl+/Br+ from Compound 5). 1 milliliter aliquots were removed from the test mixture at various predetermined times, and the active halogen was quenched by 1 milliliter portions of sterile 0.02 Normal sodium thiosulfate. Serial dilutions were made into sterile saline, and three 25 microliter aliquots of each of the resulting dilutions were applied to the dried surface of a Petri dish containing tryptic soy and nutrient agars for plating *S. aureus* and *P. aeruginosa*, respectively. After 48 hours at 37° C. the three replicates for each dilution were counted and averaged. This average was used to compute the cfu/ml for that particular aliquot. Inactivation of the organism was considered to be at least 99.9999 percent when no colonies were detected in the thiosulfate quenched aliquots.

The results of these experiments are tabulated in Table V.

EXAMPLE 16

Algaestatic Properties of Chlorinated Imidazolidin-4-ones

Two 10 gallon aquariums each containing 35 liters of Bristol's solution (described by R. C. Starr in the article "The Culture Collection of Algae at the University of Texas", *J. Phycology*, 14, 47 (1978)) at pH 6.8 were inoculated with a mixture of three species of algae; *Oscillatoria lutea*, *Anabaena cylindrica*, and *Chlorella pyrenoidosa*. The 2 aquariums were continually aerated and each illuminated by a 20 watt Gro-lux lamp placed 15 centimeters from the side of the aquarium. The experiment was conducted at ambient temperature which ranged between 21° and 24° C.

After a 34 day growth period the heavy algal cell density was measured by direct counts using a hemacytometer. The cell density in aquarium A at this time was $2.2 \times 10^7$ cells per milliliter, while that in aquarium B was $6.6 \times 10^6$ cells per milliliter. The absorbances of the two solutions at 750 nanometers were also measured at that time and found to be 0.273 for aquarium A and 0.112 for aquarium B. The absorbance at 750 nanometers has been employed as an index of algal chlorophyll concentration ("Standard methods for the Examination of Water and Wastewater", 16th edition, American Public Health Association, Washington, D.C., 1985, p. 1070). Then a solution of 1.042 grams of 1,3-dichloro-2,2,5,5-tetramethylimidazolidin-4-one (Compound 1) as prepared in example 3 in 500 milliliters of demand-free water (DFW) was added to aquarium A resulting in an initial potential positive chlorine concentration of 9.9

TABLE V

| | | PERCENT INACTIVATION OF BACTERIA | | | | | |
|---|---|---|---|---|---|---|---|
| | | Test Compound Contact Time (minutes) | | | | | |
| | | Cpd. 1 | | Cpd. 5$^a$ | | Cpd. 3 | |
| Organism | Test Conditions | 5 | 10 | 5 | 10 | 5 | 10 |
| S. aureus | pH 4.5, 22° C., DFW, 5 ppm | 99.962 | * | * | * | 87.428 | 96.316$^b$ |
| | pH 7.0, 22° C., DFW, 5 ppm | 89.134 | 99.131$^c$ | * | * | 0 | 4.42$^d$ |
| | pH 9.5, 22° C., DFW, 5 ppm | * | * | * | * | 32.653 | 50.246$^e$ |
| | pH 9.5, 4° C., DFW, 5 ppm | 71.292 | 80.897$^f$ | * | * | ND | ND |
| | pH 9.5, 4° C., SDW, 10 ppm | 43.770 | 68.090$^g$ | * | * | 2.861 | 0$^h$ |
| P. aeruginosa | pH 7.0, 22° C., DFW, 5 ppm | * | * | * | * | ND | ND |

$^a$The molar equivalent to 5 or 10 ppm total potential Cl+ in total Cl+/Br+ was employed.
$^b$A > 99.9999% inactivation was obtained after 60 minutes contact.
$^c$A > 99.9999% inactivation was obtained after 30 minutes contact.
$^d$A > 99.9999% inactivation was obtained after 588 minutes contact.
$^e$A > 99.9999% inactivation was obtained after 454 minutes contact.
$^f$A > 99.9999% inactivation was obtained after 30 minutes contact.
$^g$A > 99.9999% inactivation was obtained after 240 minutes contact.
$^h$A > 99.9999% inactivation was obtained after 2857 minutes contact.
* = > 99.9999% inactivation at the contact time indicated.
ND = No Determination
1 = 1,3-Dichloro-4,4,5,5-tetramethylimidazolidin-4-one
3 = 1-Chloro-4,4,5,5-tetramethylimidazolidin-4-one
5 = 1-Bromo-3-chloro-4,4,5,5-tetramethylimidazolidin-4-one The data of Table V demonstrate that the three halogenated imidazolidin-4-one derivatives are bactericidal to different degrees. Compound 5 caused a greater than 99.9999 percent reduction of bacteria under all conditions in less than or equal 5 minutes of contact time even in the presence of heavy halogen demand (SDW). Compound 1 was reasonably efficient as a bactericide also. Compound 3 was the least efficient, but given sufficient contact time, it also caused greater than 99.9999 percent inactivation under all conditions tested.

milligrams per liter in that aquarium. Similarly a solution of 0.872 gram of 1-chloro-2,2,5,5-tetramethylimidazolidin-4-one (Compound 3) as prepared in example 6 in 500 milliliters of DFW was added to aquarium B resulting in an initial potential positive chlorine concentration of 4.9 milligrams per liter in that aquarium. The aquariums were sampled periodically and analyzed for algal growth by means of absorbance measurements at 750 nanometers using a Milton Roy Spectronic 301 spectrophotometer and for total potential positive chlorine concentration using standard iodometric titration. It was observed during the course of the experiment that Compound 1 caused a noticeable loss of green coloration within 4 hours of its addition, and within 2 days, aquarium A showed only white turbidity resulting from the bleaching of the algae. Similar phenomena were observed for aquarium B although a longer time period for decoloration caused by Compound 3 was noted. Following the loss of all total potential positive chlorine from the aquariums, second additions of 0.87 grams of Compound 3 and of 1.042 grams of Compound 1 were made to aquariums B and A, respectively. When all titratable potential positive chlorine had disappeared from both aquariums after a total elapsed time of 19 days, the algae began to grow again as evidenced by noticeable green coloration and an increase in absorbance at 750 nanometers. Quantitataive data are presented in Table VI.

TABLE VI

Algastatic Effect of Halogenated Imidazolidin-4-ones

| | Compound | | | |
|---|---|---|---|---|
| | 1 | | 3 | |
| Time, Days | $A_{750}{}^a$ | % Cl$^{+b}$ | $A_{750}{}^a$ | % Cl$^{+b}$ |
| 0 | 0.273 | 100.0 | 0.112 | 100.0 |
| 1 | 0.064 | 82.9 | 0.063 | 71.8 |
| 3 | 0.081 | 44.4 | 0.066 | 31.0 |
| 6 | ND | 13.8 | ND | 0.0$^c$ |
| 7 | ND | 7.0 | ND | 77.3 |
| 8 | 0.058 | 3.4 | 0.021 | 47.6 |
| 10 | 0.038 | 0.0$^d$ | 0.012 | 17.3 |
| 16 | 0.020 | 34.7 | 0.007 | 0.0 |
| 19 | 0.055 | ND | 0.010 | ND |

$^a$Absorbance at 750 Nanometers
$^b$Percent Total Positive Chlorine Remaining
$^c$An Additional 0.87 Grams of Compound 3 Was Added
$^d$An Additional 1.042 Grams of Compound 1 Was Added
1 = 1,3-dichloro-2,2,5,5-tetramethylimidazolidin-4-one
3 = 1-chloro-2,2,5,5-tetramethylimidazolidin-4-one
ND = No Determination The data in Table VI plus qualitative observations noted above demonstrate that compounds 1 and 3 are both algastatic, but not algacidal, over extended periods of time for water containing heavy algal growth.

EXAMPLE 17

Prevention of the Growth of Algae in Water by 1,3-dichloro-2,2,5,5-tetramethylimidazolidin-4-one Two 10 gallon aquariums were each filled with 35 liters of Bristol's solution at pH 6.8 as described in example 16. To aquarium A was added 6.14 milligrams per liter total potential positive chlorine from 0.638 grams of 1,3-dichloro-2,2,5,5-tetramethylimidazolidin-4-one (Compound 1) as prepared in example 1. Aquarium B was used as a control with no halogenated compound added. Then 5 milliliters of an inoculum containing the algae *Oscillatoria lutea, Anabaena cylindrica*, and *Chlorella pyrenoidosa* with an absorbance of 0.14 at 750 nanometers was added to each aquarium. Constant aeration and illumination as described in example 16 were provided throughout the experiment. The laboratory temperature varied between 21° and 24° C. during the course of the experiment. Both aquariums were sampled periodically such that the absorption at 750 nanometers could be measured with a Milton Roy Spectronic 301 spectrophotometer. Aquarium A was also sampled for total potential positive chlorine using standard iodometric titration. The control aquarium B developed a noticeable green turbid tint after 7 days; aquarium A did not develop such a color at any time during the 18 day experiment. Quantitative data are tabulated in Table VII.

TABLE VII

Prevention of Algae Growth by Halogenated Imidazolidin-4-one

| | Compound 1 | | Control |
|---|---|---|---|
| Time, Days | $A_{750}{}^a$ | % Cl$^{+b}$ | $A_{750}{}^a$ |
| 0 | ND | 100.0 | ND |
| 1 | ND | 70.1 | ND |
| 4 | ND | 53.4 | ND |
| 5 | ND | 52.1 | ND |
| 6 | ND | 51.0 | ND |
| 7 | 0.002 | 49.5 | 0.009 |
| 8 | ND | 48.9 | ND |
| 11 | 0.0 | 45.8 | 0.012 |
| 12 | 0.001 | 45.6 | 0.019 |
| 13 | 0.0 | 44.8 | 0.025 |
| 14 | 0.001 | 43.3 | 0.037 |
| 15 | 0.0 | 44.8 | 0.074 |
| 18 | 0.0 | 41.9 | 0.094 |

$^a$Absorbance at 750 Nanometers
$^b$Percent Total Potential Positive Chlorine Remaining
1 = 1,3-dichloro-2,2,5,5-tetramethylimidazolidin-4-one
ND = No Determination The data in Table VII plus qualitative observations noted above demonstrate that Compound 1 is effective at preventing the growth of algae in water as long as a measurable amount of the compound is present.

EXAMPLE 18

Prevention of Growth of Algae in Water by Stoichiometric Amounts of 2,2,5,5-tetramethylimidazolidin-4-one and Free Chlorine Two 10 gallon aquariums were each filled with 35 liters of Bristol's solution at pH 6.8 as described in examples 16 and 17. To aquarium A was added 0.702 grams ($4.94 \times 10^{-3}$ moles) of 2,2,5,5-tetramethylimidazolidin-4-one (Compound 6) prepared as in example 2 in 500 milliliters of pH 7.0 demand-free water (DFW) to achieve a concentration of $1.39 \times 10^{-4}$ moles per liter of the precursor to compounds 1, 3, 4, and 5 in aquarium A. Then 326 milliliters of a pH 7.0 solution containing $9.88 \times 10^{-4}$ moles of total potential positive chlorine from free chlorine prepared by bubbling chlorine gas into buffered DFW as described in example 7 was added to aquarium A, and the mixture was allowed to react for 60 minutes to form compounds 1 and 3 in situ. A 10 milliliter aliquot of algae inocula (*Oscillatoria lutea, Anabaena cylindrica*, and *Chlorella pyrenoidosa* as in examples 16 and 17) having an absorption of 0.010 at 750 nanometers was then added to each aquarium. Constant aeration and illumination as described in examples 16 and 17 were provided throughout the experiment which was conducted in the temperature range 21°–24° C. Samples were withdrawn periodically from both aquariums for measurement of absorption at 750 nanometers using a Milton Roy Spectronic 301 spectrophotometer and from aquarium A for determination of total potential positive chlorine concentration. The amount of free chlorine was also measured after the initial 60 minute reaction period of Compound 6 and free chlorine, and 1.08 milligrams per liter were found; a small amount ($5.33 \times 10^{-4}$ moles) of Compound 6 was necessarily added at that time to completely react with all of the excess free chlorine. There was no measurable free chlorine present when the algae inoculum was added. A distinct green turbid tint was observed in the control aquarium B after 7 days. Aquarium A did not develop such a color at any time during the 27 day experiment. Quantitative data are tabulated in Table VIII.

TBLE VIII

Prevention of Algae Growth by
Unhalogenated Imidazolidin-4-one
Mixed with a Stoichiometric Amount
of Free Chlorine

| Time, Days | Compound 6 + Free Cl+ | | Control |
|---|---|---|---|
|  | $A_{750}{}^a$ | % Cl+ $^b$ | $A_{750}{}^a$ |
| 0 | ND | 100.0 | ND |
| 1 | ND | 92.5 | ND |
| 2 | ND | 90.9 | ND |
| 5 | ND | 86.7 | ND |
| 6 | ND | 85.2 | ND |
| 8 | 0.0 | 83.7 | 0.003 |
| 21 | 0.0 | 62.0 | 0.011 |
| 27 | 0.0 | 53.1 | 0.022 |

$^a$Absorbance at 750 Nanometers
$^b$Percent Total Potential Positive Chlorine Remaining
6 = 2,2,5,5-tetramethylimidazolidin-4-one
ND = No Determination The data in Table VIII plus qualitative observations noted above demonstrate that Compound 6 mixed with a stoichiometric amount of free chlorine to form compounds 1 and 3 is effective at preventing the growth of algae in water as long as a measurable amount of total potential positive halogen is present.

EXAMPLE 19

Disinfection of Hard Surfaces by Halogenated Imidazolidin-4-ones

The efficacies of compounds 1 and 5 as hard surface disinfectants were assessed by using a modification of the AOAC Use-Dilution Method as described in "Official Methods of Analysis of the Association of Official Analytical Chemists", ed. W. Horwitz, A.O.A.C., Washington, D.C., 1989, pp. 58–59. Small stainless steel cylinders (Penicylinders from Fisher Scientific) were cleaned with 1 Normal sodium hydroxide solution, sterilized in 0.1 percent asparagine in an autoclave, and cooled to ambient temperature. The cylinders were then inoculated with Staphylococcus aureus (ATCC 25923) by placing them in a 24 hour old nutrient broth culture of the organism for 15 minutes. The cylinders were aseptically removed from the broth, placed in a sterile petri dish upon filter paper for draining, and dried at 37° C. in an incubator for 60 minutes.

The halogenated imidazolidin-4-ones were dissolved in demand-free water buffered at pH 7.0 at concentrations of 25, 50, 100, and 200 parts per million of potential ionizable positive chlorine for Compound 1 (or molar equivalents of total potential ionizable positive halogen for Compound 5), and 2 milliliter aliquots of the solutions were added to each of a series of sterile culture tubes. Control solutions of pH 7.0 demand-free water were also added to a series of tubes. At least 10 tubes at each concentration of disinfectant were employed. Then an inoculated metal cylinder was added to each tube containing disinfectant and each control tube at exactly 30 second intervals. After exactly 10 minutes contact time the cylinders were removed from the tubes at 30 second intervals in the same order as was used for their addition, i.e. the contact time was 10 minutes for all cylinders. Each metal cylinder was placed into a culture tube containing 3 milliliters of nutrient broth and 0.01 normal sodium thiosulfate to quench disinfectant action. All tubes were examined for bacterial growth (inspected for the presence or absence of turbidity) following 48 hours of incubation at 37° C.

The results of this experiment were that while all control tubes exhibited bacterial growth, none of the tubes containing compounds 1 or 5 at any of the concentration levels exhibited bacterial growth. It can be concluded from these results that 1,3-dichloro-2,2,5,5-tetramethylimidazolidin-4-one (Compound 1) and 1-bromo-3-chloro-2,2,5,5-tetramethylimidazolidin-4-one (Compound 5) are effective hard surface disinfectants at concentrations at least as low as 25 parts per million of potential ionizable positive chlorine for Compound 1 and its molar equivalent (40.7 parts per million) of total potential positive halogen for Compound 5.

Although the present process has been described with reference to specific details of certain embodiments thereof, it is not intended that such details should be regarded as limitations upon the scope of the invention except as and to the extent that they are included in the accompanying claims.

What is claimed is:

1. N,N'-dihaloimidazolidin-4-one and N-haloimidazolidin-4-one represented by the graphic formula:

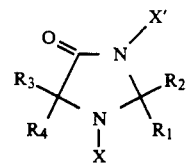

wherein X and X' are each halogen selected from the group consisting of chlorine and bromine, or one may be hydrogen while the other is halogen selected from the group chlorine and bromine; $R_1$, $R_2$, $R_3$, and $R_4$ are each selected from the group consisting of hydrogen, $C_1$–$C_4$ alkyl, $C_1$–$C_4$ alkoxy, hydroxy, phenyl, and substituted phenyl, or $R_1$, $R_2$ and/or $R_3$, $R_4$ may represent spiro-substitution selected from the group consisting of pentamethylene and tetramethylene, and mixtures thereof; provided that not more than one of the substituents $R_1$–$R_4$ is hydrogen and provided that when X is chlorine and X' is hydrogen, that not more than three of the groups $R_1$–$R_4$ are methyl.

2. N,N'-dihaloimidazolidin-4-one according to claim 1 wherein X and X' are chlorine, and the substituents $R_1$–$R_4$ are each selected from a group consisting of $C_1$–$C_3$ alkyl, $C_1$–$C_3$ alkoxy, hydroxy, phenyl, para-substituted phenyl, or $R_1$, $R_2$ and/or $R_3$, $R_4$ may represent spiro-substitution selected from the group pentamethylene and tetramethylene.

3. N,N'-dichloroimidazolidin-4-ones according to claim 2 wherein $R_1$, $R_2$, $R_3$, and $R_4$ are each selected from the group methyl and ethyl, or $R_1$, $R_2$ and/or $R_3$, $R_4$ may represent spiro-substituted pentamethylene.

4. 1,3-dichloro-2,2,5,5-tetramethylimidazolidin-4-one.

5. 1,3-dichloro-2,5 bis (pentamethylene) imidazolidin-4-one.

6. 1,3-dichloro-2-pentamethylene-5,5-dimethylimidazolidin-4-one.

7. 1,3-dichloro-2,2-dimethyl-5-pentamethyleneimidazolidin-4-one.

8. 1,3-dichloro-2,2-dimethyl-5,5-diethylimidazolidin-4-one.

9. 1,3-dichloro-2-pentamethylene-5,5-diethylimidazolidin-4-one.

10. 1,3-dichloro-2-pentamethylene-5-ethyl-5-methylimidazolidin-4-one.

11. N,N'-dihaloimidazolidin-4-one according to claim 1 wherein X and X' are bromine, and the substituents $R_1$–$R_4$ are each selected from a group consisting of $C_1$–$C_3$ alkyl, $C_1$–$C_3$ alkoxy, hydroxy, phenyl, para-substituted phenyl, or $R_1$, $R_2$ and/or $R_3$, $R_4$ may represent spiro-substitution selected from the group pentamethylene and tetramethylene.

12. N,N'-dibromoimidazolidin-4-ones according to claim 11 wherein $R_1$, $R_2$, $R_3$, and $R_4$ are each selected from the group methyl and ethyl, or $R_1$, $R_2$ and/or $R_3$, $R_4$ may represent spiro-substituted pentamethylene.

13. 1,3-dibromo-2,2,5,5-tetramethylimidazolidin-4-one.

14. 1,3-dibromo-2,5-bis (pentamethylene) imidazolidin-4-one.

15. N,N'-dihaloimidazolidin-4-one according to claim 1 wherein X is bromine and X' is chlorine or X is chlorine and X' is bromine, and the substituents $R_1$–$R_4$ are each selected from a group consisting of $C_1$–$C_3$ alkyl, $C_1$–$C_3$ alkoxy, hydroxy, phenyl, para-substituted phenyl, or $R_1$, $R_2$ and/or $R_3$, $R_4$ may represent spiro-substitution selected from the group pentamethylene and tetramethylene.

16. N-bromo-N'-chloroimidazolidin-4-ones according to claim 15 wherein $R_1$, $R_2$, $R_3$, and $R_4$ are each selected from the group methyl and ethyl, or $R_1$, $R_2$ and/or $R_3$, $R_4$ may represent spiro-substituted pentamethylene.

17. 1-bromo-3-chloro-2,2,5,5-tetramethylimidazolidin-4-one.

18. 1-bromo-3-chloro-2,5-bis(pentamethylene) imidazolidin-4-one.

19. N-chloro-N'-bromoimidazolidin-4-ones according to claim 15 wherein $R_1$, $R_2$, $R_3$, and $R_4$ are each selected from the group methyl and ethyl, or $R_1$, $R_2$ and/or $R_3$, $R_4$ may represent spiro-substituted pentamethylene.

20. 1-chloro-3-bromo-2,2,5,5-tetramethylimidazolidin-4-one.

21. 1-chloro-3-bromo-2,5-bis (pentamethylene) imidazolidin-4-one.

22. N-haloimidazolidin-4-one according to claim 1 wherein either X or X' is halogen selected from the group chlorine and bromine and the other group is hydrogen, the substituents $R_1$–$R_4$ are each selected from a group consisting of $C_1$–$C_3$ alkyl, $C_1$–$C_3$ alkoxy, hydroxy, phenyl, para-substituted phenyl, but provided that not more than three are methyl when X is chlorine and X' is hydrogen, or $R_1$, $R_2$ and/or $R_3$, $R_4$ may represent spiro-substitution selected from the group pentamethylene and tetramethylene.

23. N-chloroimidazolidin-4-one according to claim 22 wherein $R_1$, $R_2$, $R_3$, and $R_4$ are each selected from the group methyl and ethyl, but provided that not more than three are methyl when X is chlorine and X' is hydrogen, or $R_1$, $R_2$ and/or $R_3$, $R_4$ may represent spiro-substituted pentamethylene.

24. 1-chloro-2,5-bis (pentamethylene) imidazolidin-4-one.

25. 3-chloro-2,2,5,5-tetramethylimidazolidin-4-one.

26. 3-chloro-2,5-bis (pentamethylene) imidazolidin-4-one.

27. N-bromoimidazolidin-4-one according to claim 22 wherein $R_1$, $R_2$, $R_3$, and $R_4$ are each selected from the group methyl and ethyl, or $R_1$, $R_2$ and/or $R_3$, $R_4$ may represent spiro-substituted pentamethylene.

28. 1-bromo-2,2,5,5-tetramethylimidazolidin-4-one.

29. 1-bromo-2,5-bis (pentamethylene)imidazolidin-4-one.

30. 3-bromo-2,2,5,5-tetramethylimidazolidin-4-one.

31. 3-bromo-2,5-bis (pentamethylene) imidazolidin-4-one.

* * * * *